United States Patent
Kelly et al.

(10) Patent No.: US 10,703,688 B2
(45) Date of Patent: Jul. 7, 2020

(54) METHOD FOR PRODUCING ORGANIC ACIDS AND ORGANIC ACID DEGRADATION COMPOUNDS FROM BIOMASS

(71) Applicant: Georgia-Pacific LLC, Atlanta, GA (US)

(72) Inventors: John Patrick Kelly, Sugar Hill, GA (US); Michael Eugene Carroll, Loganville, GA (US); Paul Topping, Smyrna, GA (US)

(73) Assignee: Georgia-Pacific LLC, Atlanta, GA (US)

( * ) Notice: Subject to any disclaimer, the term of this patent is extended or adjusted under 35 U.S.C. 154(b) by 93 days.

(21) Appl. No.: 15/810,125

(22) Filed: Nov. 12, 2017

(65) Prior Publication Data

US 2018/0065898 A1 Mar. 8, 2018

Related U.S. Application Data

(63) Continuation of application No. 15/224,887, filed on Aug. 1, 2016, now Pat. No. 9,815,745, which is a continuation of application No. 14/487,208, filed on Sep. 16, 2014, now Pat. No. 9,403,734.

(60) Provisional application No. 61/879,656, filed on Sep. 18, 2013.

(51) Int. Cl.
*C07B 41/08* (2006.01)
*C07C 51/00* (2006.01)

(52) U.S. Cl.
CPC .............. *C07B 41/08* (2013.01); *C07C 51/00* (2013.01)

(58) Field of Classification Search
CPC ................................ C07C 51/00; C07B 41/08

USPC ......................................................... 562/515
See application file for complete search history.

(56) References Cited

U.S. PATENT DOCUMENTS

| | | | |
|---|---|---|---|
| 3,701,789 A | 10/1972 | Ramos-Rodriguez | |
| 5,608,105 A | 3/1997 | Fitzpatrick | |
| 6,054,611 A | 4/2000 | Farone et al. | |
| 6,228,177 B1 * | 5/2001 | Torget .................... | C07G 17/00 |
| | | | 127/37 |
| 2015/0052806 A1 | 2/2015 | Frey et al. | |
| 2015/0080602 A1 | 3/2015 | Kelly et al. | |

FOREIGN PATENT DOCUMENTS

| | | | | |
|---|---|---|---|---|
| WO | 98/19986 | 5/1998 | | |
| WO | WO-2013041669 A1 * | 3/2013 | ............... | C12N 1/20 |

OTHER PUBLICATIONS

"The Biofine Process—Production of Levulinic Acid, Furfural, and Formic Acid from Lignocellulosic Feedstocks", Biorefineries—Industrial Processes and Products: Status Quo and Future Directions, Wiley-VCH, Weinheim, pp. 139-164, Jan. 1, 2006.
"Comment on Processes for the Direct Conversion of Cellulosic Biomass into Levulinate Esters", ChemSusChem, vol. 3, No. 12, Nov. 18, 2010, pp. 1349-1351.
Galletti et al., BioResources, 2012, 7(2), 1824-1835.
International Search Report and Written Opinion for International Application No. PCT/US2014/05585 dated Dec. 29, 2014.

* cited by examiner

*Primary Examiner* — Yevgeny Valenrod

(57) ABSTRACT

A method and integrated reactor system are provided for producing one or more organic acids, organic acid degradation compounds, and combinations thereof, from various types of biomass, including sludge from a pulp and paper mill.

20 Claims, 2 Drawing Sheets

METHOD FOR PRODUCING ORGANIC ACIDS AND ORGANIC ACID DEGRADATION COMPOUNDS FROM BIOMASS

CROSS-REFERENCE TO RELATED APPLICATIONS

This application is a continuation of co-pending U.S. patent application Ser. No. 15/224,887, filed on Aug. 1, 2016, which is a continuation of U.S. patent application Ser. No. 14/487,208, filed on Sep. 16, 2014, now U.S. Pat. No. 9,403,734, which claims priority to U.S. Provisional Patent Application No. 61/879,656, filed on Sep. 18, 2013, which are incorporated by reference herein.

TECHNICAL FIELD

This invention relates to the hydrolysis of different types of biomass, including sludge and other lignocellulosic biomass, to form various products, including organic acids and organic acid degradation compounds.

BACKGROUND OF THE INVENTION

Pulp and paper manufacturers continually are looking for alternatives for use of waste produced during the manufacture of various paper-based products. Although some alternative disposal methods exist, there remains a need for cost effective methods to convert at least a portion of the sludge to one or more products having a higher value than use of the sludge as a combustible fuel or other commodity.

SUMMARY

Methods are provided for hydrolyzing biomass to form various products, particularly producing organic acids and organic acid degradation compounds. Generally, the methods include providing a biomass feed comprising a sludge from a pulp and paper mill including one or more six carbon chain sugars, a lignocellulosic biomass, or a combination thereof; and hydrolyzing the biomass feed to one or more organic acids, organic acid degradation compounds, or combinations thereof, in one or more reactors.

These and other features, aspects, and advantages of the present invention and embodiments thereof will become better understood when the following detailed description is read with reference to the accompanying drawing, where the components are not necessarily to scale and in which corresponding reference numerals designate corresponding parts throughout the drawings.

DETAILED DESCRIPTION OF EMBODIMENTS

Figure 1:
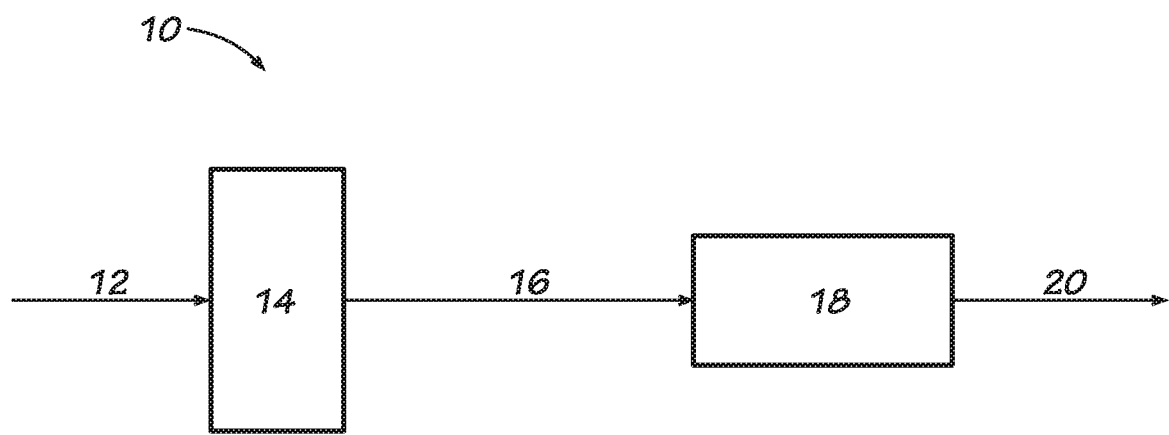
FIG. 1 is schematic diagram of an integrated reactor system for producing organic acids from sludge and lignocellulosic biomass according to an embodiment.

In the following description, numerous specific details are given to provide a thorough understanding of embodiments. The embodiments can be practiced without one or more specific details, or with other methods, components, materials, and the like. In other instances, well known structures, materials, or operations are not shown or described in detail to avoid obscuring aspects of the embodiments.

Reference throughout the specification to "one embodiment," "an embodiment," or "embodiments" means that a particular feature, structure, or characteristic described in connection with the embodiment is included in at least one embodiment. Thus, the appearances of the phases "in one embodiment" or "in an embodiment" in various places throughout the specification are not necessarily referring to the same embodiment. Furthermore, the particular features, structures, or characteristics may be combined in any suitable manner in one or more embodiments.

Methods and systems are provided for producing organic acids and organic acid degradation compounds using the sludge from a pulp and paper mill and other lignocellulosic biomass. Integration of a system for converting sludge and lignocellulosic biomass to organic acids and organic acid degradation compounds into an existing pulp and paper mill in accordance with embodiments of this disclosure may allow the production of organic acids or other valuable products with less capital investment and operating expense, and may provide operating cost savings in addition to producing a valuable product.

Generally described, the methods include providing a biomass feed comprising sludge from a pulp and paper mill including one or more six carbon chain sugars, a lignocellulosic biomass, or a combination thereof; and hydrolyzing the biomass feed in one or more reactors. In one embodiment, the step of hydrolyzing the biomass feed comprises at least partially hydrolyzing the biomass feed to convert one or more six carbon chain compound precursors to one or more six carbon chain sugars and, subsequently, converting the one or more six carbon chain sugars to one or more organic acids, organic acid degradation compounds, or combinations thereof (individually or collectively referred to hereafter as the "organic acid compounds"). Non-limiting examples of organic acid compounds include levulinic acid, formic acid, acetic acid, propionic acid, and the like.

The biomass feed may be converted to organic acid compounds in one or more reactors using either a continuous or batch process. In addition, various types of biomass feed may be added to the process streams or one or more reactors in a variety of locations. For example, in embodiments the biomass feed includes both sludge and a lignocellulosic biomass that may be mixed to form a biomass feed stream to a first reactor that at least partially hydrolyzes the lignocellulosic biomass and may partially convert the one or more six carbon chain sugars in the sludge to one or more organic acid compounds. In embodiments, the sludge and lignocellulosic biomass may be added separately to the first reactor. In embodiments, the lignocellulosic biomass may be partially hydrolyzed in the first reactor without the sludge, and the sludge may be combined with the partially hydrolyzed lignocellulosic biomass from the first reactor to form a partially hydrolyzed biomass feed stream for a second reactor to convert the one or more six carbon chain sugars in the partially hydrolyzed biomass feed stream to one or more organic acid compounds. In embodiments, the sludge and partially hydrolyzed lignocellulosic biomass may be added separately to the second reactor. In still other embodiments, the sludge and lignocellulosic biomass may be treated in reactors in parallel or in series.

The step of at least partially hydrolyzing the biomass feed may comprise contacting the biomass feed with steam, a combination of steam and at least one acid, alcohol, or a combination of alcohol and at least one acid. For example, in embodiments the step of at least partially hydrolyzing the biomass feed is performed at a temperature in the range of 150° C. to about 250° C., about 170° C. to about 240° C., about 170° C. to about 230° C., about 170° C. to about 220° C., or about 180° C. to about 210° C. In embodiments, the step of at least partially hydrolyzing the biomass feed may be carried out in a first reactor at a temperature of about 170° C. to about 190° C. for about 35 minutes to about 60 minutes. In embodiments, the first reactor is a tubular reactor with axial mixing, such as a continuous stirred-tank reactor (CSTR). In certain embodiments, the partially hydrolyzed biomass feed comprising the one or more six carbon chain sugars may be the desired product and may be used, for example, in various microbiological processes known to those skilled in the art (e.g., as a feed for microorganisms).

The conversion of the one or more six carbon chain sugars in the biomass feed or partially hydrolyzed biomass feed may be carried out in the same reactor as the partial hydrolysis of the biomass feed. For example, the conversion of one or more six carbon chain sugars in sludge to organic acid compounds occurs very rapidly (on the order of seconds), while the hydrolysis of lignocellulosic biomass requires a longer residence time (on the order of 30 to 60 minutes). In such embodiments the reactor system and operating conditions desirably are configured to maximize the conversion of the one or more six carbon chain sugars in the sludge to one or more organic acid compounds while minimizing the degradation of any desired organic acid compounds formed from the conversion of the sludge in the first reactor.

The conversion of the partially hydrolyzed biomass feed may then be conducted in the same reactor or in a second reactor in series with the first reactor. The step of converting the one or more six carbon chain sugars generally is performed at a temperature in the range of about 150° C. to about 250° C. that is greater than the temperature used for partially hydrolyzing the biomass feed. For example, in embodiments the step of converting the one or more six carbon chain sugars is conducted at a temperature of about 190° C. to about 220° C. for about 1 minute to about 15 minutes. While the step of converting the one or more six carbon chain sugars may be conducted in the same reactor as pre-hydrolysis, in embodiments the conversion is conducted in a second reactor comprising a tubular reactor with substantially no axial mixing, such as a plug flow reactor (PFR).

Sludge

As used herein, "sludge" refers to the residues that result from pulp and papermaking, and generally is recovered from wastewater streams of pulp and paper mills. The sludge may be a primary sludge, secondary sludge, recycle mill sludge, or blend of sludges, preferably obtained from pulp and paper mills. In embodiments, the sludge is an effluent stream from a pulp and paper mill, such as the whitewater stream of a pulp and paper mill. In embodiments, the sludge is recovered from the whitewater stream upstream of a primary clarifier in a pulp and paper mill or downstream of a primary clarifier and upstream of a secondary clarifier in a pulp and paper mill.

The composition of the sludge will vary depending on the raw material, process, and final product being manufactured. Generally, the sludge includes from 5 to 50% solids primarily including cellulose and other six carbon chain sugars. The solids content of the sludge optionally may be increased using one or more dewatering processes before the sludge is introduced into the integrated reactor systems described herein. For example, in embodiments the solids content of the sludge may be increased to about 20% prior to being diluted with acid before or after being added to the integrated reactor system.

Lignocellulosic Biomass

Suitable lignocellulosic biomass materials for producing organic acid compounds generally include one or more six carbon chain compound precursors. The six carbon chain compound precursor or precursors can be converted to six carbon chain sugars. Desirably, the six carbon chain compound precursor or precursors are from the hemicellulose portion of a lignocellulosic biomass. Examples of suitable lignocellulosic biomass materials include any biological materials comprising lignocellulose that includes six carbon chain compound precursors, such as wood from trees, wood chips, slash or hog fuel from wood tree processing, forest residue, straw, chaff, grain, grasses, corn, corn husk, weeds, aquatic plants, and hay, and lignocellulose containing material of biological origin, such as some municipal waste or household waste.

Some lignocellulosic biomass materials have a higher six carbon chain sugar content for a greater yield of desired organic acid compounds; therefore, selection of higher six carbon chain sugar content lignocellulosic biomass can result in higher organic acid compound yields and efficiency. For example, southern softwood includes a greater concentration of six carbon chain compounds in the hemicellulose portion than does hardwood. Therefore, southern softwood enables a higher yield of six carbon organic acid compounds than does hardwood biomass.

If necessary, the particle size of the lignocellulosic biomass material can be reduced before introduction into the reaction system. Any manner known to be suitable to the skilled person can be used to reduce the particle size or otherwise increase the surface area of the lignocellulosic biomass material. Examples of such methods include crushing, grinding, milling, cutting, chipping, shredding, granulation, fibrillation, steam explosion, and any combination thereof.

Although not shown separately, the feed system can include a turpentine extractor to remove turpentine from wood biomass. The structure and operation of turpentine extractors are well known to those skilled in the art.

Reactor Systems

FIG. 1 is a schematic diagram of an embodiment of a reactor system 10 for producing organic acid compounds from a sludge and lignocellulosic biomass. The system 10 includes a biomass feed stream 12 for introducing a lignocellulosic biomass and sludge to a first reactor 14. According to an embodiment, the first reactor 14 partially hydrolyzes the lignocellulosic biomass to form a first phase comprising partially hydrolyzed lignocelluosic biomass comprising cellulose and lignin and a second phase comprising one or more five carbon chain sugars and one or more six carbon chain sugars from degradation of hemicellulose in the lignocellulosic biomass. Additionally, the first reactor 14 converts at least a portion of the sludge to one or more organic acid compounds.

According to an embodiment, the hydrolyzing of the biomass feed stream may comprise contacting the biomass feed stream in the first reactor with one or more of steam, at least one acid, or at least one alcohol. Suitable acids include mineral acids such as hydrochloric acid, nitric acid, phosphoric acid, sulfuric acid, and the like, and organic acids such as acetic acid, formic acid, and the like. According to embodiments, the acid may be added to the biomass feed stream in an amount from about 0 to about 10% by weight of the biomass feed stream. According to an embodiment, the mineral acid may be formed from a precursor, such as sulfur dioxide, added to the biomass feed stream. Suitable alcohols include methanol, ethanol, propanol, butanol, and the like.

The reaction parameters for the hydrolysis in the first reactor can be set to favor the production of the one or more five and six carbon chain sugars from the biomass feed as opposed to a higher order reaction conversion, such as to tar or char, while also reducing the degradation of any organic acid compounds that are formed. In accordance with an embodiment, the hydrolysis in the first reactor is conducted at a temperature of about 150° C. to about 250° C., about 170° C. to about 195° C., or about 170° C. to about 185° C. for a residence time of about 35 minutes to about 60 minutes or about 35 to 45 minutes.

The first reactor can be any type of reactor known to be suitable to those skilled in the art and optionally may include a pre-steaming device that receives the biomass feed stream and steam to heat the lignocellulosic biomass and sludge and begin the hydrolysis. The steam heated biomass feed stream is fed to or near the top of a vertical tube reactor. More steam and optionally acid or alcohol, as described hereinabove, is added to the biomass in the vertical tube reactor and the biomass is hydrolyzed as it passes from the top to the bottom of the reactor.

The first phase produced by hydrolysis in the first reactor is substantially solid and the second phase is substantially liquid and includes a solvent such as water or alcohol or both and any acid or alcohol used in the hydrolysis. This mixture of the first phase and the second phase optionally may be fed to a separator which separates the first phase from the second phase. The separator can be of a type known to those skilled in the art to be suitable for this purpose, non-limiting examples of which include a screw press, a belt press, a drum filter, a disc filter, or a centrifuge, or the like. Alternatively, the first and second phases may be introduced into a second reactor for further hydrolysis and conversion of the partially hydrolyzed biomass into organic acid compounds.

In an embodiment, the first phase comprising the partially hydrolyzed biomass, which includes cellulose and lignin, may be delivered to a wood pulp product production system (described more herein below) or introduced into a second reactor for further hydrolysis. According to an embodiment, the second phase from the separator optionally may be fed to a different separator in which the solvent and acid are separated from the second phase by liquid-liquid extraction and returned as recycled solvent and acid to the first reactor.

The partially hydrolyzed biomass, particularly the five and six carbon chain sugars, then may be fed from the first reactor, or optionally from the separator, to a second reactor and optionally one or more subsequent reactors for converting at least a portion of the one or more five carbon chain sugars and one or more six carbon chain sugars from the second phase into various products, such one or more organic acid compounds. The reaction products then may be separated using methods known in the art.

In embodiments, the second reactor can be any reactor suitable to one skilled in the art for this purpose, non-limiting examples of which include an autoclave, a PFR, a batch reactor, or a CSTR. According to an embodiment, the second reactor is operated at a relatively low temperature and has a relatively low residence time. The reaction parameters of the second reactor can be set to favor the conversion of the one or more six carbon chain sugars from the second phase primarily to one or more desired organic acid compounds, and to avoid conversion of the one or more five carbon chain sugars from the second phase. For example, in embodiments the step of converting at least a portion of the one or more six carbon chain sugars is carried out in the second reactor at a temperature of about in the conversion reaction system is carried out at a temperature of about 150° C. to about 250° C., about 180° C. to about 230° C., or about 200° C. to about 210° C. at a pressure high enough so that the reactor contents do not reach their boiling point, such as about 10 psi above the vapor pressure of the liquid in the reactor, for a residence time of about 1 minute to about 15 minutes.

According to an embodiment, an acid such as a mineral acid or organic acid is added to the second reactor to convert the partially hydrolyzed biomass to one or more organic acid compounds. Suitable mineral acids include hydrochloric acid, nitric acid, sulfuric acid, phosphoric acid, and the like, and suitable organic acids include, acetic acid, formic acid, and the like, and may be added to the partially hydrolyzed biomass in the second reactor in an amount of from about 0 to about 10% by weight of the reactor contents or more depending on parameters such as the type of biomass, the particular acid, the temperature in the reactor and the like.

According to an embodiment, the resulting product stream, which may be a mixture of one or more organic acid compounds and tar, may be transferred to a separator for the removal of one or more organic acid compounds. Any suitable separation system known to those skilled in the art can be used to separate the one or more organic acid compounds from the resulting product stream. According to embodiments, methods of separation include those such as liquid-liquid extraction, gas stripping, steam stripping, distillation and the like. The one or more organic acid compounds can then be captured in a condenser, purified in a purifier, and stored in a storage container.

According to an embodiment, a mixture of the one or more organic acid compounds and solvent and any acid used in the second reactor may be fed from the second reactor to a liquid-liquid extraction system for separating the one or more organic acid compounds from the solvent and acid. According to embodiments of this disclosure, other methods of separation include those such as gas stripping, steam stripping, distillation, and the like. The one or more organic acid compounds can then be stored in appropriate storage containers. The solvent and acid can be recovered and recycled via conduit for use in other operations. In some embodiments, the mixture fed to the extraction distillation system may include other residual substances which may also be separated and stored in a residual substance container. Such residual substance can also be used as a combustion fuel to produce heat.

Organic acid compounds are useful in a variety of processes, including synthesis of polymers, pharmaceuticals, and chemical commodities such as methyltetrahydrofuran, valerolactone, and ethyl levulinate.

Integration of the above-described method for producing organic acid compounds from biomass, including sludge and lignocellulosic biomass, in a pulp and paper mill provides several advantages. For example, in such a process the amount of waste streams requiring disposal by landfill or other less economically beneficial means may be decreased while the production of a higher value product, such as the one or more organic acid compounds, may increase the profitability of the overall process.

Figure 2:
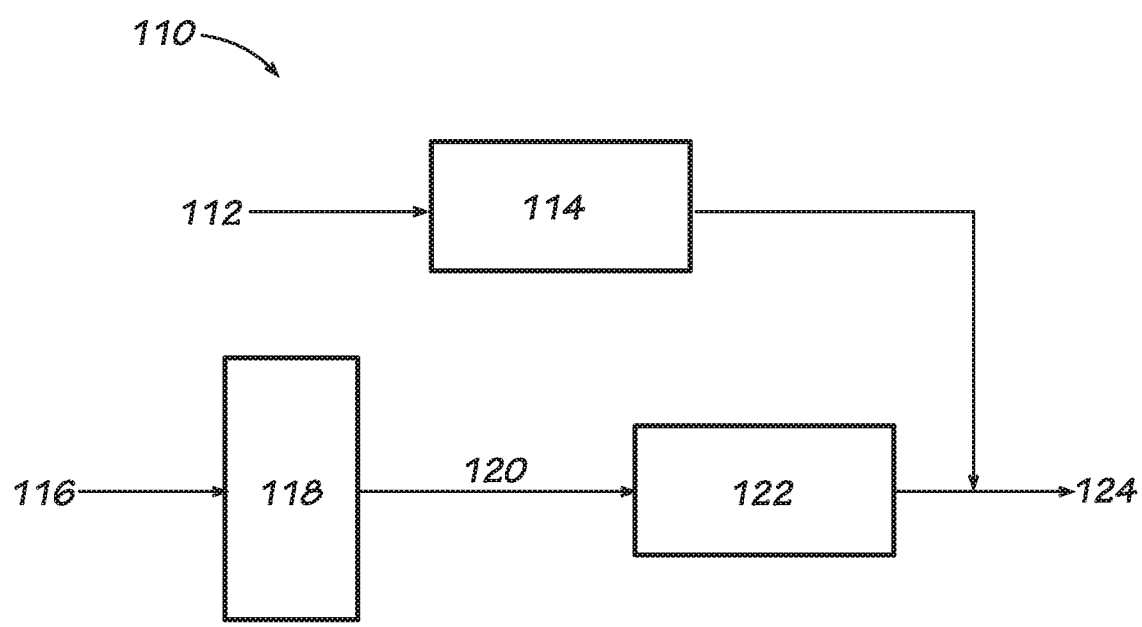
FIG. 2 is schematic diagram of an integrated reactor system for producing organic acids from sludge and lignocellulosic biomass according to an embodiment.

According to another embodiment illustrated in the schematic of FIG. 2, the reactor system includes one or more reactors for converting the sludge to one or more organic acid compounds in parallel with one or more reactors for converting the lignocellulosic biomass to one or more organic acid compounds. For example, the reactor system 110 may include a sludge reactor 114 for converting a sludge feed stream 112 to one or more organic acid compounds 124 in parallel with a first reactor 118 to partially hydrolyze a lignocellulosic biomass feed stream 116 to form a partially hydrolyzed lignocellulosic biomass stream 120, and a second reactor 122 to convert the partially hydrolyzed lignocellulosic biomass stream 120 to one or more organic acid compounds 124.

Figure 3:
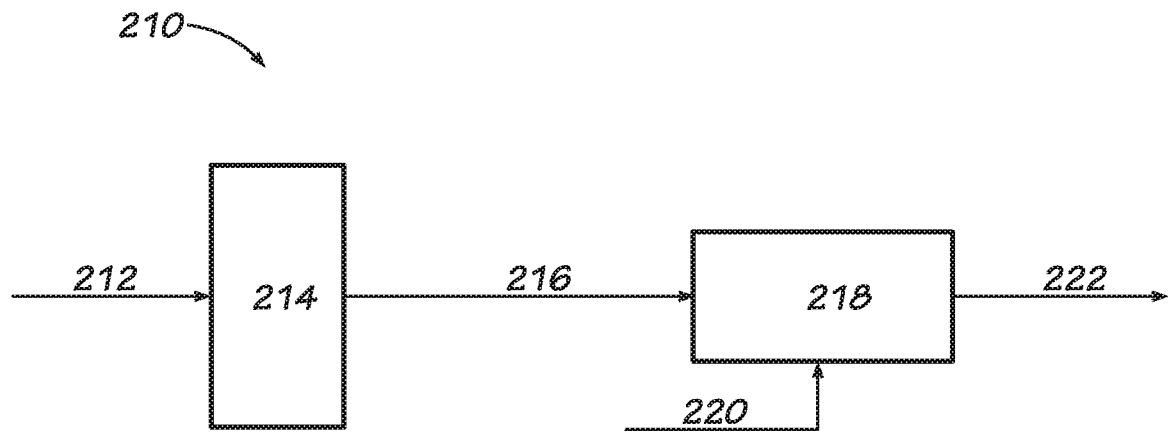
FIG. 3 is schematic diagram of an integrated reactor system for producing organic acids from sludge and lignocellulosic biomass according to an embodiment.

In still another embodiment illustrated in the schematic of FIG. 3, the reactor system 210 includes a first reactor 214 for partially hydrolyzing the lignocellulosic biomass feed stream 212 to form a partially hydrolyzed lignocellulosic biomass stream 216 that is subsequently introduced into a second reactor 218. The sludge 220 may be separately introduced into the second reactor 218, where both the partially hydrolyzed lignocellulosic biomass stream 216 and sludge 220 are converted into one or more organic acid compounds 222.

Figure 4:
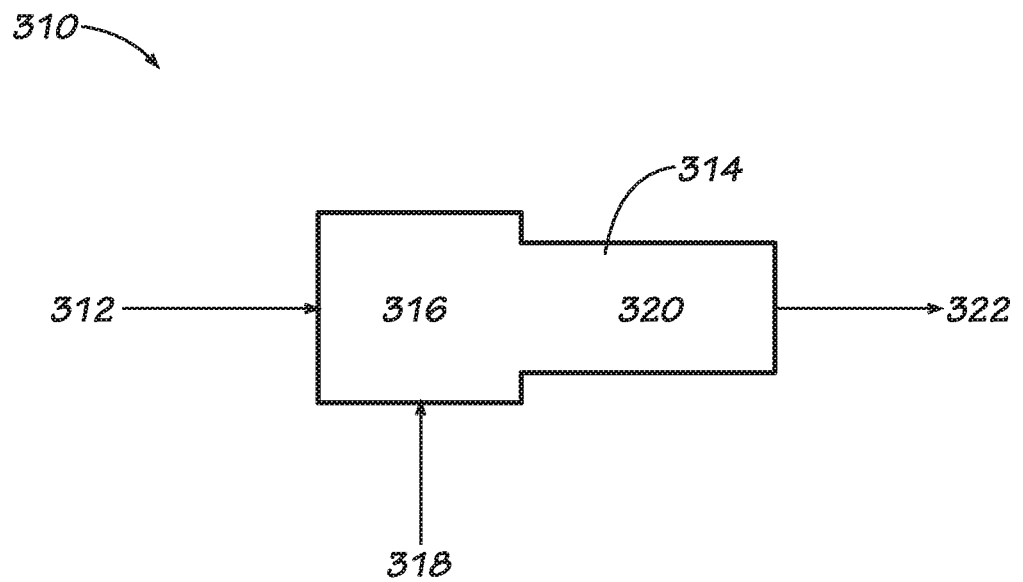
FIG. 4 is schematic diagram of an integrated reactor system for producing organic acids from sludge and lignocellulosic biomass according to an embodiment.

In still another embodiment illustrated in the schematic of FIG. 4, the reactor system 310 includes a reactor 314 for partially hydrolyzing a lignocellulosic biomass feed stream 312 in a first zone 316. A separate, sludge feed stream 318 may introduce the sludge into the first zone 316 (as illustrated) or downstream of the first zone in a second zone 320 (not shown), where the conversion of the partially hydrolyzed lignocellulosic biomass to one or more organic acid compounds 322 occurs.

In each of the above configurations, it should be noted that the reaction time for conversion of the sludge into one or more organic acid compounds is significantly less than that required for conversion of other lignocellulosic biomass, such as wood chips, into such products. Because of the disparity of reaction times, the reactor configuration and operating conditions should be optimized to increase conversion of the lignocellulosic biomass to one or more six carbon sugar chains without degrading any of the one or more organic acid compounds that are formed from the conversion of sludge in embodiments in which the biomass of the reactor includes both a lignocellulosic biomass and sludge. In such embodiments it can be advantageous to utilize a larger reactor that is operated at a lower temperature (i.e., such as a CSTR) as a first reactor followed by a smaller reactor that is operated at a higher temperature (i.e., such as a PFR).

It should be apparent that the foregoing relates only to embodiments of the present invention and that numerous changes and modifications can be made herein without departing from the scope of the invention as defined by the following claims and equivalents thereof.

What is claimed is:

1. A process for producing one or more organic acids, comprising:
    contacting a lignocellulosic biomass comprising a six carbon chain sugar precursor with steam to heat the lignocellulosic biomass to a temperature of about 150° C. to about 250° C. within a tubular reactor with axial mixing to produce an at least partially hydrolyzed lignocellulosic biomass comprising a six carbon chain sugar;
    heating the at least partially hydrolyzed lignocellulosic biomass comprising the six carbon chain sugar to a temperature of about 150° C. to about 250° C. within a plug flow reactor to convert the six carbon chain sugar to a first product comprising a first organic acid;
    heating a sludge from a pulp and paper mill comprising an additional six carbon chain sugar to convert the additional six carbon chain sugar to a second product comprising a second organic acid; and
    mixing the first product and the second product to produce a combined product.

2. The process of claim 1, wherein the first organic acid comprises levulinic acid, formic acid, acetic acid, propionic acid, or a mixture thereof, and wherein the second organic acid comprises levulinic acid, formic acid, acetic acid, propionic acid, or a mixture thereof.

3. The process of claim 1, wherein the lignocellulosic biomass is further contacted with a mineral acid, an alcohol, or a mixture thereof to produce the at least partially hydrolyzed lignocellulosic biomass.

4. The process of claim 3, wherein the lignocellulosic biomass is contacted with the mineral acid, and wherein the mineral acid is present in an amount of up to 10% by weight of the lignocellulosic biomass.

5. The process of claim 1, wherein the lignocellulosic biomass is further contacted with an alcohol and heated to a temperature of about 170° C. to about 195° C. for about 35 minutes to about 45 minutes to produce the at least partially hydrolyzed lignocellulosic biomass.

6. The process of claim 1, wherein the at least partially hydrolyzed lignocellulosic biomass comprising the six carbon chain sugar is heated to a temperature of about 190° C. to about 220° C. to convert the six carbon chain sugar to the first product comprising the first organic acid.

7. The process of claim 1, wherein:
    the lignocellulosic biomass is further contacted with a mineral acid, an alcohol, or a mixture thereof and heated to a temperature of about 170° C. to about 230° C. to produce the at least partially hydrolyzed lignocellulosic biomass, and
    the at least partially hydrolyzed lignocellulosic biomass is heated to a temperature of about 190° C. to about 220° C. to convert the six carbon chain sugar to the first product comprising the first organic acid.

8. The process of claim 1, wherein:
    the lignocellulosic biomass is further contacted with a mineral acid, an alcohol, or a mixture thereof and heated to a temperature of about 170° C. to about 230° C. for about 35 minutes to about 45 minutes to produce the at least partially hydrolyzed lignocellulosic biomass,
    the at least partially hydrolyzed lignocellulosic biomass is heated to a temperature of about 190° C. to about 220° C. for about 1 minute to about 15 minutes to convert the six carbon chain sugar to the first product,
    the first product further comprises tar, and
    the first organic acid comprises levulinic acid.

9. The process of claim 1, wherein:
    the lignocellulosic biomass is further contacted with a mineral acid,
    the lignocellulose biomass is heated to a temperature of about 170° C. to about 230° C. for about 35 minutes to about 60 minutes to produce the at least partially hydrolyzed lignocellulosic biomass,
    the mineral acid is present in an amount of up to 10% by weight of the lignocellulosic biomass, the at least partially hydrolyzed lignocellulosic biomass is heated to a temperature of about 190° C. to about 220° C. for about 1 minute to about 15 minutes to convert the six carbon chain sugar to the first product, the first product further comprises tar, the first organic acid comprises levulinic acid, and the sludge is heated to a temperature of about 190° C. to about 220° C. to convert the additional six carbon chain sugar to the second product comprising the second organic acid.

10. A process for producing levulinic acid, comprising:

contacting a lignocellulosic biomass comprising a six carbon chain sugar precursor with steam to heat the lignocellulosic biomass to a temperature of about 170° C. to about 230° C. within a tubular reactor with axial mixing to produce an at least partially hydrolyzed lignocellulosic biomass comprising a six carbon chain sugar;

contacting the at least partially hydrolyzed lignocellulosic biomass with a first mineral acid and heating the at least partially hydrolyzed lignocellulosic biomass to a temperature of about 150° C. to about 250° C. within a plug flow reactor to convert the six carbon chain sugar to a first product comprising levulinic acid and tar;

heating a sludge from a pulp and paper mill comprising an additional six carbon chain sugar to convert the additional six carbon chain sugar to a second product comprising levulinic acid and tar;

mixing the first product and the second product to produce a combined product; and separating the levulinic acid from the tar to produce a purified levulinic acid product.

11. The process of claim 10, further comprising contacting the lignocellulose biomass with a second mineral acid, wherein:

the second mineral acid is present in an amount of up to 10% by weight of the lignocellulosic biomass, the lignocellulosic biomass is heated to the temperature of about 170° C. to about 230° C. for about 35 minutes to about 60 minutes to produce the at least partially hydrolyzed lignocellulosic biomass, the first mineral acid is present in an amount of up to 10% by weight of the at least partially hydrolyzed lignocellulosic biomass, the at least partially hydrolyzed lignocellulosic biomass is heated to a temperature of about 190° C. to about 220° C. for about 1 minute to about 15 minutes to convert the six carbon chain sugar to the first product, and the sludge is heated to a temperature of about 190° C. to about 220° C. to convert the additional six carbon chain sugar to the second product.

12. A process for producing one or more organic acids, comprising:

introducing a heated mixture comprising steam and a lignocellulosic biomass comprising a six carbon chain sugar precursor to a first reactor, wherein the first reactor comprises a tubular reactor with axial mixing;

at least partially hydrolyzing the lignocellulosic biomass within the first reactor to produce an at least partially hydrolyzed lignocellulosic biomass comprising a six carbon chain sugar;

introducing the at least partially hydrolyzed lignocellulosic biomass to a second reactor, wherein the second reactor comprises a plug flow reactor;

heating the at least partially hydrolyzed lignocellulosic biomass within the second reactor to a temperature of about 150° C. to about 250° C. to produce a first product comprising a first organic acid;

introducing a sludge from a pulp and paper mill comprising an additional six carbon chain sugar to a third reactor; and heating the sludge within the third reactor to a temperature of about 150° C. to about 250° C. to produce a second product comprising a second organic acid.

13. The process of claim 12, further comprising combining the first product and the second product to produce a combined product, wherein the first organic acid comprises levulinic acid, formic acid, acetic acid, propionic acid, or a mixture thereof, and wherein the second organic acid comprises levulinic acid, formic acid, acetic acid, propionic acid, or a mixture thereof.

14. The process of claim 12, wherein the at least partially hydrolyzed lignocellulosic biomass is heated to a temperature of about 190° C. to about 250° C. for about 1 minute to about 15 minutes to produce the first product.

15. The process of claim 14, wherein the first product further comprises tar, and wherein the first organic acid comprises levulinic acid.

16. The process of claim 1, wherein the at least partially hydrolyzed lignocellulosic biomass comprises a first phase and a second phase, wherein the first phase is substantially solid and comprises the at least partially hydrolyzed lignocellulosic biomass, and the second phase is substantially liquid and comprises water, and wherein:

the first phase is separated from the second phase, and the first phase is heated to convert the six carbon chain sugar to the first product.

17. The process of claim 16, wherein the at least partially hydrolyzed lignocellulosic biomass further comprises an acid, wherein the second phase further comprises the acid, and wherein the acid is separated from the water by liquid-liquid extraction.

18. The process of claim 1, wherein the tubular reactor is a continuous stirred-tank reactor.

19. The process of claim 10, wherein the tubular reactor is a continuous stirred-tank reactor.

20. The process of claim 12, wherein the tubular reactor is a continuous stirred-tank reactor.

* * * * *